(12) United States Patent
Veggeland et al.

(10) Patent No.: US 9,549,999 B2
(45) Date of Patent: Jan. 24, 2017

(54) RADIOPHARMACEUTICAL COMPOSITION

(75) Inventors: Janne Veggeland, Oslo (NO); Grethe Karin Madsen, Oslo (NO); Stig Hemsted, Oslo (NO)

(73) Assignee: GE Healthcare Limited (GB)

( * ) Notice: Subject to any disclaimer, the term of this patent is extended or adjusted under 35 U.S.C. 154(b) by 537 days.

(21) Appl. No.: 12/677,528

(22) PCT Filed: Sep. 19, 2008

(86) PCT No.: PCT/EP2008/062528
§ 371 (c)(1),
(2), (4) Date: Mar. 11, 2010

(87) PCT Pub. No.: WO2009/037336
PCT Pub. Date: Mar. 26, 2009

(65) Prior Publication Data
US 2010/0236958 A1 Sep. 23, 2010

Related U.S. Application Data

(60) Provisional application No. 60/974,089, filed on Sep. 21, 2007.

(30) Foreign Application Priority Data

Sep. 21, 2007 (GB) .................................. 0718386.6

(51) Int. Cl.
| | | |
|---|---|---|
| *A61K 51/00* | (2006.01) |
| *A61M 36/14* | (2006.01) |
| *A61K 51/04* | (2006.01) |
| *A61K 51/02* | (2006.01) |
| *A61K 31/66* | (2006.01) |
| *A61K 9/00* | (2006.01) |
| *A61K 47/22* | (2006.01) |

(52) U.S. Cl.
CPC ............. *A61K 51/04* (2013.01); *A61K 9/0019* (2013.01); *A61K 31/66* (2013.01); *A61K 47/22* (2013.01); *A61K 51/00* (2013.01); *A61K 51/025* (2013.01)

(58) Field of Classification Search
CPC ...................................................... A61K 51/00
See application file for complete search history.

(56) References Cited

U.S. PATENT DOCUMENTS

| | | | | |
|---|---|---|---|---|
| 4,066,183 | A * | 1/1978 | Armstrong ..................... | 215/247 |
| 4,364,920 | A * | 12/1982 | Winchell ..................... | 424/1.53 |
| 4,677,175 | A * | 6/1987 | Ihara et al. ................... | 526/254 |
| 6,713,042 | B2 * | 3/2004 | Liu .............................. | 424/1.65 |
| 6,770,259 | B2 * | 8/2004 | Carpenter, Jr. ............... | 424/9.1 |
| 7,052,672 | B2 * | 5/2006 | Forster et al. ................ | 424/1.65 |
| 2006/0120956 | A1 * | 6/2006 | Kopka et al. ................. | 424/1.11 |

FOREIGN PATENT DOCUMENTS

| | | |
|---|---|---|
| JP | 2001178814 | 7/2001 |
| WO | 02/053192 | 7/2002 |
| WO | 2006/064175 | 6/2006 |
| WO | 2007/148088 | 12/2007 |

OTHER PUBLICATIONS

Myoview Nyomed Amersham 1998.*
Ponto ("Preparation and Dispensing Problems Associated with Technetium Tc-99m Radiopharmaceuticals", Correspondence Continuing Education Courses for Nuclear Pharmacists and Nuclear Medicine Professionals, vol. 11, Lesson 1, The University of New Mexico Health Sciences Center College of Pharmacy Albuquerque, New Mexico, 2004).*
Graham et al. (Nucl. Med. Comm. 1997, 18, 335; abstract 48.).*
Bartosch, et.al. "Adsorption of Technetium-99M Tetrofosmin and Technetium-99M Furifosmin on Plastic Syringes" European Journal of Nuclear Medicine Sep. 1998, vol. 25, No. 9, Sep. 1998, pp. 1333-1335.
Gunasekera, et.al. "Adsorption of Radiopharmaceuticals to Syringes Leads to Lower Administered Activity Thank Intended" Nuclear Medicine Communications, vol. 22, No. 5, May 2001, pp. 493-497.
Kislowksy, et.al. "Evaluation of the Stability of (99M)TC-ECD and Stabilized (99M)TC-HMPAO Stored in Syringes" Journal of Nuclear Medicine Technology Dec. 2001, vol. 29, No. 4, Dec. 2001, pp. 197-200.
Jansson, et.al. "Adsoprtion of Some Technetium-99M Radiopharmaceuticals Onto Disposable Plastic Syringes" Journal of Nuclear Medicine Technology Sep. 1998, vol. 26, No. 3, Sep. 1998, pp. 196-199.
Stopar, et.al. "Adsorption of Radiopharmaceuticals to Syringes: Setting Up a Reliable Protocol for Its Assessment" Nuclear Medicine Communications Dec. 2007, vol. 28, No. 12, Dec. 2007, pp. 951-955.
Murray, et.al. "Technetium-99M-Tetrofosmin: Retention of Nitrogen Atmosphere in Kit Vial As a Cause of Poor Quality Material" Nuclear Medicine Communications, Lippincott Williams and Wilkins, XX vol. 21, No. 9, Sep. 1, 2000, pp. 845-849.
Yigit, et.al. "Preparation of TC-99M Labeled Vitamin C (Ascorbic Acid) and Biodistribution in Rats" Chemical & Pharmaceutical Bulleting (Tokyo), vol. 54, No. 1, Jan. 2006 pp. 1-3.
Liu, et.al. "Ascorbic Acid: Useful As a Buffer Agent and Radiolytic Stabilizer for Metalloradiopharmaceuticals" Bioconjugate Chemistry, vol. 14, No. 5, Sep. 2003, pp. 1052-1056.

(Continued)

*Primary Examiner* — Michael G Hartley
*Assistant Examiner* — Melissa Perreira
(74) *Attorney, Agent, or Firm* — Wood IP LLC

(57) ABSTRACT

The present invention provides a $^{99m}$Tc-tetrofosmin radiopharmaceutical composition comprising tetrofosmin and a radioprotectant at a particular range of molar ratios. A kit and a multi-dose kit for the preparation of the radiopharmaceutical composition of the invention are also provided, as well as a process for the preparation of multiple unit patient doses of the radiopharmaceutical composition and a unit dose of the radiopharmaceutical composition.

13 Claims, No Drawings

(56) References Cited

OTHER PUBLICATIONS

Vucina "[Radiochemical Purity and Stability of TC-99M-Pyrophosphate]" Medicinski Pregled Sep.-Oct. 2000, vol. 53, No. 9-10, Sep. 2000, pp. 502-505.
GB0718386.6 Search Report Dated Jan. 21, 2008.
PCT/EP2008/062528 ISRWO Dated Jul. 13, 2009.
SAITO, Polymer vol. 41, No. 11, 1992 pp. 770-773.

* cited by examiner

RADIOPHARMACEUTICAL COMPOSITION

This application is a filing under 35 U.S.C. 371 of international application number PCT/EP2008/062528, filed Sep. 19, 2008, which claims priority to Great Britain application number 0718386.6 filed Sep. 21, 2007, and U.S. Provisional application number 60/974,089 filed Sep. 21, 2007, the entire disclosure of each of which is hereby incorporated by reference.

TECHNICAL FIELD OF THE INVENTION

The present invention relates to an improved radiopharmaceutical composition. Specifically, the invention relates to a radiopharmaceutical composition comprising $^{99m}$Tc-tetrofosmin.

DESCRIPTION OF RELATED ART

In vivo imaging radiopharmaceuticals based on the radioisotope technetium-99m ($^{99m}$Tc) are known for a variety of clinical applications, including functional studies (e.g. renal), and perfusion studies (especially heart and brain). The radioisotope $^{99m}$Tc has a half-life of 6 hours, such that $^{99m}$Tc radiopharmaceuticals are usually prepared shortly before use from so-called "kits".

These kits for the preparation of $^{99m}$Tc radiopharmaceuticals permit the user to maintain stocks of non-radioactive, lyophilised vials containing the necessary reactants, which are designed to be reconstituted with $^{99m}$Tc-pertechnetate ($TcO_4^-$) from a supply of $^{99m}$Tc to give the desired sterile $^{99m}$Tc radiopharmaceutical in a facile manner. A sterile solution of $^{99m}$Tc-pertechnetate in isotonic saline is obtained by elution of a technetium generator with sterile saline, as is known in the art.

Kits for the preparation of $^{99m}$Tc radiopharmaceuticals typically contain:
(i) a ligand which forms a metal complex with $^{99m}$Tc,
(ii) a biocompatible reducing agent capable of reducing pertechnetate, i.e. Tc(VII) to the lower oxidation state of the desired $^{99m}$Tc metal complex product.

The biocompatible reducing agent for the $^{99m}$Tc pertechnetate is typically stannous ion, i.e. Sn(II). The kit may contain additional excipients, such as weak chelating agents (e.g. gluconate, glucoheptonate, tartrate, phosphonate or EDTA); stabilisers; pH-adjusting agents; buffers; solubilisers or bulking agents (such as mannitol, inositol sodium hydrogen carbonate or sodium chloride), to facilitate handling and lyophilisation of the kit components. To facilitate storage and distribution, the non-radioactive kits are usually supplied freeze-dried in a sterile vial with closure. The lyophilised formulation also permits facile reconstitution by the end users with sterile $^{99m}$Tc-pertechnetate in saline, to give the desired sterile, injectable $^{99m}$Tc radiopharmaceutical for human use. The shelf life of the non-radioactive technetium kit may be several months.

Radiopharmaceuticals are routinely administered by means of disposable clinical grade syringes, which are typically made of plastic. It is known that incomplete delivery of radiopharmaceuticals can occur due to adsorption of the radiopharmaceutical to the surfaces with which it comes into contact during preparation for injection, including the surface of the syringe. An unwanted consequence is reduction in the injected activity. This can lead to insufficient radioactivity in the injected dose, and thereby necessitate preparation of a higher activity sample with the undesirable consequence of increased radiation exposure during preparation. It is therefore clear that adsorption of the radiopharmaceutical should be minimised. A particular radiopharmaceutical known to adsorb to disposable clinical grade syringes is $^{99m}$Tc-tetrofosmin, and a number of studies have evaluated this phenomenon.

Bartosch et al (1998 Eur. J. Nuc. Med. 25(9) pp 1333-5) investigated retention of $^{99m}$Tc-tetrofosmin in reconstituted Myoview™ onto 2 ml disposable plastic syringes that were obtained from Henke Sass Wolf GmbH. In these syringes the highest measured value for retention of $^{99m}$Tc-tetrofosmin was found to be around 5% following 30 minutes storage in the syringe.

In another study, various brands of disposable plastic syringe were compared for residual activity of several commonly-used radiopharmaceuticals (Gunaskera et al 1996 J. Nuc. Med. 23 p 1250 & 2001 Nuc. Med. Comm. 22 pp 493-497). This study demonstrated that the amount of binding of $^{99m}$Tc-tetrofosmin in reconstituted Myoview™ varies considerably depending on the brand of syringe. For example, reduced binding of $^{99m}$Tc-tetrofosmin was observed to Braun (~6%) compared with Becton-Dickinson (~30%) and Sherwood (~16%) disposable syringes after 30 minutes in the syringe. Confirmation of this variability was demonstrated in a further analysis of the adsorption of $^{99m}$Tc-tetrofosmin in reconstituted Myoview™ onto 2 ml disposable plastic syringes (Jansson et al 1998 J. Nuc. Med. Technol. 26 pp 196-9). This study found reduced binding of $^{99m}$Tc-tetrofosmin to Braun Injekt disposable syringes (~3%) as compared with Becton-Dickinson Discardit (~8%), Cordan Once (~15%) and Becton-Dickinson Plastipak (~22%), disposable syringes, in that order.

In order to overcome the problem of high adsorption of $^{99m}$Tc-tetrofosmin with certain disposable syringe types a solution would be to prescribe that particular syringe types be used for the administration of $^{99m}$Tc-tetrofosmin. However, given that there will be a certain amount of variability between batches even for a particular syringe type, it would also be reasonable to assume that variable adsorption would occur from batch to batch with the same syringe type. It would therefore be preferable to have a solution accessible with any batch of any syringe type so that hospitals and radiophaimacies would not have to alter their preferred methods of preparation. Reduction of retained activity for all syringe types would be advantageous.

The Myoview™ kit is a 10 ml vial containing the lyophilised formulation:

| | |
|---|---|
| Tetrofosmin | 0.23 mg |
| Stannous chloride dihydrate | 30 μg |
| Disodium sulfosalicylate | 0.32 mg |
| Sodium-D-gluconate | 1.0 mg |
| Sodium hydrogen carbonate | 1.8 mg |
| pH on reconstitution | 8.3-9.1, | which is sealed under nitrogen gas USP/NF in a 10 ml glass vial, which upon reconstitution with Sterile Sodium ($^{99m}$Tc) Pertecnetate Injection USP/Ph. Eur., yields a solution containing the heart imaging radiopharmaceutical $^{99m}$Tc tetrofosmin. The molar concentration of tetrofosmin will vary depending on the reconstitution volume. When reconstituted as per the manufacturer's instructions (package leaflet) the volume used to reconstitute the lyophilised Myoview™ formulation is in the range 4-8 ml. This provides a maximum molar concentration of 0.15 mM tetrofosmin (1M tetrofosmin=382.45 g/L).

Another commercially available version of Myoview™ is a ready-to-inject or "conjugate" presentation, which has been on sale in Japan since 1997. This "conjugate" form comprises the pre-formed $^{99m}$Tc-tetrofosmin technetium complex in an aqueous solution in a syringe-vial, i.e. a vial with separate plunger and needle, which is designed to be readily assembled to give a syringe containing the radiopharmaceutical. The Myoview™ "conjugate" solution contains tetrofosmin at a concentration of 0.14 mg/ml (0.37 mM) and ascorbic acid at a concentration of 1.36 mg/ml (7.7 mM). The molar ratio of tetrofosmin:ascorbic acid in this formulation is therefore 0.05:1.0.

WO 2002/053192 describes a stabilised $^{99m}$Tc radiopharmaceutical formulation comprising a $^{99m}$Tc metal complex. This kit differs from the standard Myoview™ kit in that it also includes a radioprotectant as well as an antimicrobial preservative. The radioprotectant is selected from ascorbic acid, para-aminobenzoic acid and gentisic acid. The antimicrobial preservative is a paraben of the following formula:

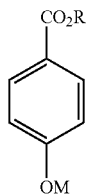

wherein R is $C_{1-4}$ alkyl and M is H or a biocompatible cation. WO 2002/053192 teaches that when the $^{99m}$Tc radiopharmaceutical is Myoview™ and the radioprotectant is ascorbic acid, the ascorbic acid is present in the range 0.4 to 1.5 mg/cm$^3$ (2.5 to 10 mM). The experimental examples of WO 2002/053192 teach a radiopharmaceutical composition comprising $^{99m}$Tc-tetrofosmin having molar ratio of tetrofosmin to ascorbic acid of around 0.045:1.0.

In WO 2006/064175 a Myoview™ kit is provided comprising a radioprotectant chosen from ascorbic acid or a salt thereof with a biocompatible cation. For ascorbic acid, a suitable concentration range is disclosed as 0.05 to 100 mg/cm$^3$ (or 0.28 to 568 mM), with a preferred range of 0.2 to 10 mg/cm$^3$ (1.14 to 57 mM), and a most preferred range of 0.4 to 1.5 mg/cm$^3$ (2.5 to 10 mM). In the experimental examples of WO 2006/064175, a molar ratio of tetrofosmin to ascorbic acid of around 0.06:1.0 is taught, which is of a similar magnitude to that taught by WO 2002/053192.

The present investigators have now found that retained activity of $^{99m}$Tc-tetrofosmin on certain disposable plastic syringes for the formulation exemplified by WO 2006/064175was unacceptably high (20 to 25%). The problem solved by the present invention is to provide an ascorbate-stabilised tetrofosmin formulation having acceptable retained activity on various clinical grade plastic syringes of $^{99m}$Tc-tetrofosmin in the reconstituted radiopharmaceutical composition.

SUMMARY OF THE INVENTION

The present invention provides a $^{99m}$Tc-tetrofosmin radiopharmaceutical composition comprising tetrofosmin and a radioprotectant at a particular range of molar ratios. A kit and a multi-dose kit for the preparation of the radiopharmaceutical composition of the invention are also provided, as well as a process for the preparation of multiple unit patient doses of the radiopharmaceutical composition and a unit dose of the radiopharmaceutical composition.

DETAILED DESCRIPTION OF THE INVENTION

Radiopharmaceutical Composition

In one aspect, the present invention provides a radiopharmaceutical composition comprising:
(i) the $^{99m}$Tc complex of tetrofosmin in a biocompatible carrier;
(ii) tetrofosmin; and,
(iii) a radioprotectant chosen from ascorbic acid or a salt thereof with a biocompatible cation;
wherein the molar ratio of tetrofosmin to radioprotectant is in the range 0.10:1.0 to 1.0:1.0.

The phrase "the molar ratio of tetrofosmin to radioprotectant" as used herein refers to the ratio of the molar concentration of total tetrofosmin in the radiopharmaceutical composition. The term "total tetrofosmin" means the sum of tetrofosmin complexed to $^{99m}$Tc, plus uncomplexed tetrofosmin, i.e. the sum of (i) and (ii) above.

The term "radiopharmaceutical" is a term well known to the person skilled in the art of nuclear medicine. The majority of radiopharmaceuticals are used for in vivo imaging, and comprise a radionuclide having emissions suitable for detection, typically by single-photon emission computed tomography (SPECT) or positron emission tomography (PET). Such a radionuclide together with a biocompatible carrier, in a form suitable for mammalian administration is a "radiopharmaceutical composition". See the "Handbook of Radiopharmaceuticals" (Welch & Redvanly, Eds. Wiley 2003) for an overview of radiopharmaceuticals, and in particular pages 329 and 530 where $^{99m}$Tc-tetrofosmin is specifically discussed.

By the term "tetrofosmin" is meant the ether-substituted diphosphine chelating agent 1,2-bis[bis(2-Ethoxyethyl)phosphino)]ethane, shown:

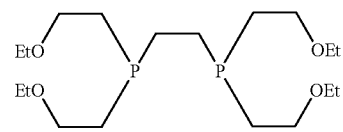

which is used in the commercial $^{99m}$Tc kit for the preparation of $^{99m}$Tc-tetrofosmin, i.e. $^{99m}$Tc(O)$_2$(tetrofosmin)$_2^+$ called Myoview™ (GE Healthcare). Tetrofosmin can be prepared as described by Chen et al (Zhong. Heyix. Zazhi 1997; 17(1): 13-15) or Reid et al (Synth. Appl. Isotop. Lab. Comp. 2000; Vol 7: 252-255). The usual synthesis involves first preparing 1,2-bis(phosphino)ethane or H$_2$PCH$_2$CH$_2$PH$_2$, followed by free radical addition of excess ethyl vinyl ether using a free radical initiator as described in Example 1.

A "biocompatible carrier" is a fluid, especially a liquid, in which the radiopharmaceutical is suspended or dissolved, such that the composition is physiologically tolerable, i.e. can be administered without toxicity or undue discomfort. The biocompatible carrier is suitably an injectable carrier liquid such as sterile, pyrogen-free water for injection; an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethylene glycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The biocompatible carrier preferably comprises an aqueous solvent, and most preferably comprises isotonic saline solution.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from ascorbic acid and salts thereof with a biocompatible cation.

By the term "biocompatible cation" is meant a positively charged counterion which forms a salt with an ionised, negatively charged anionic group, where said positively charged counterion is also non-toxic at the required dosage and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

A preferred radioprotectant is ascorbic acid. Preferably, the molar ratio of tetrofosmin to ascorbic acid is in the range 0.2:1.0 to 1.0:1.0, most preferably 0.2:1.0 to 0.5:1.0, most especially preferably 0.3:1.0 to 0.5:1.0 and in particular 0.4:1.0 to 0.5:1.0. Non-limiting examples of some preferred molar ratios of tetrofosmin to ascorbic acid are 0.14:1.0, 0.21:1.0, 0.32:1.0 and 0.47:1.0.

The radiopharmaceutical composition may optionally further comprise additional components such as a biocompatible reductant, a pH adjusting agent, transchelator or filler.

By the term "biocompatible reductant" is meant a reducing agent suitable for reduction of Tc(VII) pertechnetate to lower oxidation states of technetium, which is non-toxic at the required dosage and hence suitable for administration to the mammalian body, especially the human body. Suitable such reductants include: sodium dithionite, sodium bisulphite, ascorbic acid, formamidine sulphinic acid, stannous ion, Fe(II) or Cu(I). The biocompatible reductant is preferably a stannous salt such as stannous chloride or stannous tartrate.

The term "pH-adjusting agent" means a compound or mixture of compounds useful to ensure that the pH of the radiopharmaceutical composition is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. A preferred pH-adjusting agent for the radiopharmaceutical composition of the present invention is sodium bicarbonate.

A "transchelator" is a compound which reacts rapidly to form a weak complex with technetium, then is displaced by the ligand. This minimises the risk of formation of reduced hydrolysed technetium (RHT) due to rapid reduction of pertechnetate competing with technetium complexation. Suitable such transchelators are salts of organic acids with a biocompatible cation, especially "weak organic acids" having a pKa in the range 3 to 7. Suitable such weak organic acids are acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of gluconic acid, with a biocompatible cation, especially sodium gluconate. An additional preferred transchelator is 5-sulfosalicyclic acid or salt thereof with a biocompatible cation. Two or more transchelators may be used in combination, and the radiopharmaceutical composition of the present invention most preferably comprises a combination of sodium 5-sulfosalicyclate (SSA) and sodium gluconate. An advantage of SSA is that it also acts as a radioprotectant, thereby facilitating a reduction in the amount of ascorbic acid in the radiopharmaceutical composition while maintaining satisfactory radiolabelling, radiochemical purity, and stability post-preparation. It is believed that the increased SSA results in an increased scavenger effect as SSA scavenges hydroxy radicals in the same way as ascorbic acid does. Furthermore, SSA can be easily incorporated by use of tetrofosmin-SSA as a starting material. SSA is preferably present in the radiopharmaceutical composition of the invention in a molar ratio to ascorbic acid of between 0.15:1.0 and 0.4:1.0. Preferably, the ratio of SSA to ascorbic acid is in the range 016:1.0 to 0.37:1.0, most preferably 0.24:1.0 to 0.37:1.0.

By the term "filler" is meant a pharmaceutically acceptable bulking agent which may facilitate material handling during production of a lyophilised kit for the preparation of the radiopharmaceutical composition of the present invention. Suitable fillers include inorganic salts such as sodium chloride, and water soluble sugars or sugar alcohols such as sucrose, maltose, mannitol or trehalose. Certain pH-adjusting agents may also function as bulking agents. A preferred such dual-function filler is sodium bicarbonate. Preferred kits for the preparation of the radiopharmaceutical composition of the present invention comprise a filler to facilitate lyophilisation. A preferred such filler is the dual function filler sodium bicarbonate.

The following advantages are provided by the radiopharmaceutical composition of the invention:
(i) reduced retained activity to a range of clinical-grade plastic syringes;
(ii) improved radiochemical stability compared with known radioprotectant-containing $^{99m}$Tc tetrofosmin compositions; and,
(iii) improved radiochemical purity compared with known $^{99m}$Tc tetrofosmin compositions.

Example 2 analyses the adsorption to plastic syringes (Becton Dickinson Luer-Lok™ 3 ml) of radioactivity for compositions prepared with lyophilised formulations having molar ratios of tetrofosmin to ascorbic acid in the range of the present invention. An acceptable amount of retained activity to the plastic syringe was observed for all formulations analysed.

Example 3 demonstrates acceptable adsorption to plastic syringes with formulations encompassed by the present invention, along with excellent associated radiochemical purity (RCP) values.

Example 4 demonstrates that the characteristics found in the laboratory can be reproduced in the radiopharmacy. A formulation of the present invention has been shown to have better adhesion properties along with improved RCP in comparison with the known Myoview™ formulation.

A millimolar (mM) concentration is such that 1.0 mM equals 0.001M. The concentration of tetrofosmin in the radiopharmaceutical composition of the invention is preferably in the range 0.08-0.40 mM, most preferably 0.10-0.20 mM, and most especially preferably 0.12 to 0.18 mM. When the radioprotectant is ascorbic acid, the millimolar concentration of radioprotectant is preferably in the range 0.30-0.60 mM, most preferably in the range 0.38-0.57 mM.

The concentration of ascorbic acid in the radiopharmaceutical composition of the present invention is significantly less relative to the concentration of tetrofosmin as compared with prior art ascorbic acid-containing $^{99m}$Tc-tetrofosmin compositions. The present inventors have found that, as ascorbic acid is an acid, the amount of pH adjusting agent needs to be adjusted to ensure that the optimum pH of the kit is maintained for (i) $^{99m}$Tc radiolabelling of tetrofosmin, (ii) post-reconstitution stability, and (iii) suitability for patient administration. Radiopharmaceutical compositions are preferably formulated such that the pH of the solution in water or saline is 8.0 to 9.2, most preferably 8.0 to 8.6. It follows that less ascorbic acid in the composition requires less pH adjustment.

When the radiopharmaceutical composition of this invention is administered to a human being, a suitable amount of radioactivity to be used is in the range from 150 to 1500 MBq (4-40 mCi) per dose. For heart imaging, when rest and stress injections are administered on the same day, the first dose should be 185-444 MBq (5-12 mCi), followed by a second dose of 555-1221 MBq (15-33 mCi) given approximately 1 to 4 hours later. Hence, the initial $^{99m}$Tc activity in the $^{99m}$Tc-tetrofosmin composition of the present invention is in the range 0.2 to 100 GBq per vial, which permits multiple dosing from the same preparation even after allowing for radioactive decay of $^{99m}$Tc.

Non-Radioactive Kit

Another aspect of the present invention is a non-radioactive kit for the preparation of the radiopharmaceutical composition of the invention, said kit comprising a suitable container having a formulation contained therein, said formulation comprising:
  (i) tetrofosmin;
  (ii) a radioprotectant chosen from ascorbic acid or a salt thereof with a biocompatible cation; and,
  (iii) a biocompatible reductant;
  wherein the molar ratio of tetrofosmin to radioprotectant is as defined above for the radiopharmaceutical composition of the invention.

For the kit of the invention, the terms "tetrofosmin", "radioprotectant", "biocompatible cation", and "biocompatible reductant" and preferred embodiments thereof are as defined above for the radiopharmaceutical composition.

A "suitable container" for use in the kit of the invention is one which does not interact with any components of the radiopharmaceutical formulation of the invention, permits maintenance of sterile integrity, plus allows for an inert headspace gas (e.g. nitrogen or argon), whilst also permitting addition and withdrawal of solutions by syringe. Such containers are preferably liquid-tight ampoules and vials, the seal being provided by a liquid-tight or gas-tight closure such as a lid, stopper, or septum. A most preferred such container is a septum-sealed vial, wherein the gas-tight closure is crimped on with an overseal (typically of aluminium). Such containers have the additional advantage that the closure can withstand vacuum if desired, for example to change the headspace gas or degas solutions and can withstand an overpressure, for example to aid in the removal of the solution from the container. The gas-tight seal is suitable for multiple puncturing with a hypodermic needle. A preferred such container is a pharmaceutical grade vial. The vial is suitably made of a pharmaceutical grade material, typically glass or plastic, preferably glass. The glass of the container may optionally be coated to suppress leachables from the glass, as is known in the art. A preferred such coating is silica ($SiO_2$). Pharmaceutical grade glass vials which are coated with high purity silica are commercially available from Schott Glaswerke AG, and other suppliers.

In a preferred embodiment, the container of the kit is provided with a closure suitable for puncturing with a hypodermic needle whilst maintaining seal integrity, wherein said closure is coated on those of its surface(s) which are in contact with the container contents with a coating comprising ethylene-tetrafluoroethylene copolymer (ETFE) or modified versions thereof. The "modified versions" are those commercialised by Dalkyo Seiko as Fluorotec™. The coating is preferably a film which is laminated onto the closure, preferably at a thickness in the range 0.01-0.2 mm. Such closures are described in WO 2007/148088.

The closure body as distinct from the coating thereon, is preferably made of a synthetic, elastomeric polymer. The closure body is preferably made of chlorinated or brominated butyl rubber, or neoprene, since such polymers have low oxygen permeability. The closure body is most preferably made of chlorinated butyl rubber.

Suitable closures for use in the kit of the present invention are commercially available from West Pharmaceutical Services Inc. (www.westpharma.com, 101 Gordon Drive, PO Box 645 Lionville, Pa. 19341, USA) or Dalkyo Seiko Ltd (38-2 Sumida 3-Chome, Sumida-Ku, Tokyo, 131-0031, Japan) and have the modified ETFE coating Fluorotec™. A preferred closure is the D21 series from Dalkyo Seiko. A preferred vial closure from that series has the configuration V10 F451 W, and chlorobutyl rubber formulation denoted D21-7S. The present inventors found that for a preferred vial closure there was no leakage of radioactivity after 4-30 penetrations of the closure. Furthermore, the amount of radioactivity remaining in a preferred vial closure was less than 0.1% for vials reconstituted with 55 Gbq/30 ml and 5,5 BBq/5 ml.

Autoclaving is used in conventional pharmaceutical practice, but the closures of the kit of the present invention are preferably sterilised by gamma irradiation. That is because autoclaving leaves traces of residual moisture within the closure, and for $^{99m}$Tc-tetrofosmin it is strongly preferred to suppress the moisture content of the closure.

The non-radioactive kit may optionally further comprise additional components such as a pH adjusting agent, transchelator or filler, as defined above.

Preferably, the formulation is present in the kit in lyophilised form. The term "lyophilised" has the conventional meaning, i.e. a freeze-dried composition, preferably one which is prepared in a sterile manner. The present investigators have noted that the visual appearance of the freeze-dried cake compared with prior art ascorbic acid-containing $^{99m}$Tc-tetrofosmin was improved by decreasing the amount of ascorbic acid. This is believed to be due to the low glass-transition temperature of ascorbic acid (−54° C.), which probably reduces the glass-transition temperature of the formulation.

In a preferred embodiment, tetrofosmin is introduced to the kit formulation as tetrofosmin-SSA.

Multi-Dose Kit

In a preferred embodiment, the kit of the invention is a multi-dose kit. This "multi-dose kit" comprises the formulation of the invention in a sealed, sterile container fitted with a closure with permits addition and withdrawal of solutions such that 4 to 30 unit patient doses of $^{99m}$Tc-tetrofosmin radiopharmaceutical can be obtained from a single multi-dose kit. The preferred aspects of the container and the closure of the multi-dose kit are as provided above for the kit of the invention.

The multi-dose kit has to be sufficiently robust to withstand significantly higher levels of radioactivity, and also greater volumes of solution than the conventional Myoview™ kit. Containers for the multi-dose vial are suitably of 20 to 50 cm$^3$ volume, preferably 20 to 40 cm$^3$, most preferably 30 cm$^3$.

The multi-dose kit comprises sufficient material for multiple patient doses (e.g. up to 100 GBq of $^{99m}$Tc per vial), whereby unit patient doses can thus be withdrawn into clinical grade syringes at various time intervals during the viable lifetime of the stabilised preparation to suit the clinical situation. The unit dose of $^{99m}$Tc-tetrofosmin radiopharmaceutical may alternatively be provided in a sealed container, as described above. The term "unit patient dose" or "unit dose" means a $^{99m}$Tc-tetrofosmin radiopharmaceutical composition having a $^{99m}$Tc radioactive content suitable for in vivo imaging after administration to a single patient. Such "unit doses" are described further in an additional aspect of the invention (below). The multi-dose kits of the present invention are formulated to be suitable for obtaining 4 to 30, preferably 6 to 24 such unit doses of $^{99m}$Tc-tetrofosmin radiopharmaceutical in a reproducible manner for a range of $^{99m}$Tc generator eluates. It will, however, be possible to use the multi-dose kit to give 1 to 40, and perhaps even more than 40 such unit doses.

As described in WO 2006/064175, there are advantages associated with a multi-dose kit. A multi-dose kit needs no air addition step in the reconstitution protocol, which is an important advantage. A multi-dose kit also permits much more rapid preparation times for multiple $^{99m}$Tc-tetrofosmin radiopharmaceutical preparations, with substantially reduced operator radiation dose. A multi-dose kit also exhibits increased shelf-life stability of at least 78 weeks, whereas the conventional Myoview™ kit has a shelf-life stability of 37 weeks. Further advantages of a multi-dose kit are described in the method for preparation of multiple doses described below.

In an especially preferred embodiment, the multi-dose kit of the invention comprises the following formulation:

| | |
|---|---|
| tetrofosmin | 1.38-2.07 mg |
| stannous chloride dihydrate | 0.09 mg |
| disodium sulfosalicylate | 1.92-2.88 mg |
| sodium D-gluconate | 3.0 mg |
| sodium hydrogen carbonate | 11 mg |
| ascorbic acid | 2.0-3.0 mg |
| pH on reconstitution with saline | 8.0 to 9.1 | which is designed to be reconstituted with up to 30 ml of eluate from a $^{99m}$Tc generator.

In one especially preferred multi-dose kit formulation the tetrofosmin, disodium sulfosalicylate and ascorbic acid are included using 3.0 mg each of tetrofosmin-SSA and ascorbic acid as starting materials. Alternatively, 4.5 mg of tetrofosmin-SSA and either 2.0 or 3.0 mg ascorbic acid may be used as starting materials.

Method for Preparation of Multiple Unit Patient Doses

Another aspect of the invention is a process for the preparation of multiple unit patient doses of the radiopharmaceutical $^{99m}$Tc-tetrofosmin, which comprises:
(i) reconstituting the multidose kit of the invention with either a sterile solution of $^{99m}$Tc-pertecnetate or first a biocompatible carrier followed by a sterile solution of $^{99m}$Tc-pertecnetate;
(ii) optionally carrying out step (i) in the presence of an antimicrobial preservative;
(iii) allowing $^{99m}$Tc-tetrofosmin complex formation to take place to give a solution comprising a bulk supply of the desired $^{99m}$Tc-tetrofosmin radiopharmaceutical;
(iv) optionally checking the radiochemical purity of the bulk supply of the $^{99m}$Tc-tetrofosmin complex;
(v) withdrawing a unit dose from the bulk supply of step (iii) into a suitable syringe or container;
(vi) repeating step (v) with an additional syringe or container at later times to give further unit doses.

The unit dose for this aspect of the invention is as defined earlier in the specification, and is described more fully as a further aspect of the invention below. The biocompatible carrier and preferred embodiments thereof for this aspect of the invention are as already defined herein. A preferred biocompatible carrier for this process is sterile saline solution.

The process is preferably carried out in the absence of an antimicrobial preservative.

The sterile solution of $^{99m}$Tc-pertechnetate is preferably obtained from a technetium generator. The radioactive content of $^{99m}$Tc-pertechnetate to be used in step (i) is suitably in the range 0.2 to 100 GBq, preferably to 5 to 75 GBq. The radioactive concentration of $^{99m}$Tc is preferably no more than 10 GBq/cm$^3$, most preferably no more than 2.5 GBq/cm$^3$. Once prepared, the bulk supply of the desired $^{99m}$Tc tetrofosmin radiopharmaceutical has a usable shelf-life of up to 12 hours.

$^{99m}$Tc tetrofosmin complex formation, i.e. step (iii), is normally complete within 15 minutes at room temperature.

The process of the present invention has the advantages over the alternative of reconstituting multiple individual Myoview™ 10 ml vials that:
(a) the $^{99m}$Tc-tetrofosmin prepared exhibits reduced adhesion of to disposable plastic syringes;
(b) the number of manipulations involving radioactivity ($^{99m}$Tc-pertechnetate) is significantly reduced;
(c) no air addition step is necessary;
(d) only a single QC determination per batch of unit doses should be needed as opposed to a QC determination per dose;
(e) the bulk vial is formulated in such a way that the formulation can withstand a range of $^{99m}$Tc generator eluate conditions;
(f) fewer steps are involved, so automation is more facile; and,
(g) fewer non-radioactive kit vials are needed, so fridge storage space is saved.

The key consequences are reduced adsorption of radioactivity, reduced operator processing time (i.e. efficiency), and reduced operator radiation dose, which are more substantial the greater the number of unit doses that are to be prepared.

Unit Dose

The invention also provides a unit dose of the radiopharmaceutical $^{99m}$Tc-tetrofosmin which comprises the radiopharmaceutical composition of the invention, having a $^{99m}$Tc radioactive content suitable for imaging a single patient.

The unit patient dose is as defined above in connection with the multi-dose kit of the invention, and is provided in a sterile form suitable for human administration in a suitable container or syringe. Such syringes are suitable for clinical use and preferably disposable so that the syringe would only ever be used with an individual patient. The syringe may optionally be provided with a syringe shield to protect the operator from radiation dose. Suitable such radiopharmaceutical syringe shields are commercially available and preferably comprise either lead or tungsten, as described by Logan (1993 J. Nucl. Med. Technol. 21(3) pp 167-170).

The unit dose of $^{99m}$Tc-tetrofosmin radiopharmaceutical may alternatively be provided in a container which has a seal which is suitable for multiple puncturing with a hypodermic needle (e.g. a crimped-on septum seal closure). The unit dose of the present invention is preferably supplied in a clinical grade syringe, and is most preferably fitted with a syringe shield.

The $^{99m}$Tc radioactive content of the unit dose is suitably 150 to 1500 MBq (4-40 mCi), preferably 185 to 1250 MBq (5-34 mCi). When rest and stress injections are administered on the same day, the first dose should be 185 to 450 MBq (5-12 mCi), followed 1 to 4 hours later with a second dose of 550 to 1250 MBq (15-34 mCi). The preferred compositions employed in the unit dose are as described above for the radiopharmaceutical composition of the invention.

The invention is illustrated by the following non-limiting Examples:

BRIEF DESCRIPTION OF THE EXAMPLES

Example 1 describes the synthesis of tetrofosmin.

Example 2 compares adsorption of $^{99m}$Tc-tetrofosmin to plastic syringes for formulations having varying concentrations of tetrofosmin, ascorbic acid and sodium hydrogen carbonate. A significant reduction in retained activity on the syringes was obtained by increasing the amount of tetrofosmin in the formulation.

Example 3 compares adsorption of $^{99m}$Tc-tetrofosmin to plastic syringes for formulations having varying concentrations of tetrofosmin and ascorbic acid. Increasing the amount of tetrofosmin reduces the amount of retained activity in syringes by 2-5 percentage points (around 20-35% reduction in retained activity). The RCP after 24 hours is slightly better for samples containing 3 mg tetrofosmin per 30 ml vial, indicating that increasing the amount of tetrofosmin sulphosalicylic acid made it possible to reduce the amount of ascorbic acid without compromising the RCP.

Example 4 compares adsorption of $^{99m}$Tc-tetrofosmin to plastic syringes of Myoview™ and a multi-dose formulation of the invention in a radiopharmacy setting. Results were consistent between two radiopharmacies. The retained activity, 6-12 hours post reconstitution, is 6-12% for the formulation of the invention when 1.0 ml is drawn into the syringe. For Myoview™ the remaining activity is 12-15% when tested at similar lab conditions. The reconstituted formulation of the invention has thus better retained activity properties compared to Myoview™.

Abbreviations And Definitions

| | |
|---|---|
| AA | Ascorbic acid |
| AIBN | α-Azo-isobutyronitrile |
| BD | Becton Dickinson |
| ITLC | instant thin layer chromatography |
| PC | Paper chromatography |
| Post reconstitution | After addition of the radioactive solution |
| RAC | Radioactive concentration, GBq/ml (mCi/ml) |
| RCP | Radiochemical purity |
| Reconstitution | The process of preparing $^{99m}$Tc tetrofosmin by addition of Sterile Saline followed by addition of Sterile Sodium ($^{99m}$Tc)Pertechnetate Injection USP |
| Retained activity | Radioactivity from reconstituted Myoview formulations retained in the syringes after emptying |
| RHT | Reduced hydrolysed technetium |
| Saline | 0.9% aqueous sodium chloride solution, generator saline |
| USP | United States Pharmacopoeia |
| Vent needle | Ventilation needle to avoid overpressure in the vials when adding 30 ml. Used Drytec needle 20G. |
| WFI | Water for injection |

Materials

| Material | Manufacturer |
|---|---|
| BD PrecisionGlide 3 ml syringe | Becton Dickinson |
| Instant Imager Chromatogram Scanner | Packard |
| Ion Chamber, CRC 15R | Canberra |
| BD Microlance ™3, 21G 1½ -Nr.2. | Becton Dickinson |
| Pall ITLC SG | Pall International |
| Saline for injections, Ph. Eur | Drytec accessory and saline from TechneLite for elution of the TechneLite generator. |
| Stoppers for N58 vials | Red stopper: pH 701/45 AS and grey stopper D21-7S West Pharmaceuticals |
| Whatman no. 1 PC strip | Whatman |

EXAMPLES

Example 1

Synthesis of Tetrofosmin

All reactions and manipulations were performed either in vacuo or under an oxygen-free nitrogen atmosphere. Solvents were dried, and degassed by nitrogen purge prior to use. α-Azo-isobutyronitrile (AIBN) and ethyl vinyl ether were obtained from BDH and Aldrich respectively. Bis (diphosphino)ethane was prepared according to the literature (Inorganic Synthesis, Vol 14, 10).

A Fischer pressure-bottle equipped with a Teflon™ stirring bar, was charged with ethyl vinyl ether (5 cm$^3$, 52.3 mmol), bis(diphosphino)ethane (1 cm$^3$, 10 mmol) and α-azo-isobutyronitrile (0.1 g, 0.61 mmol). The reaction mixture was then stirred and heated to 75° C. for 16 hours. After cooling back to room temperature, the viscous liquid was transferred to a 50 cm$^3$ round-bottomed flask. Removal of volatile materials was performed by heating under vacuum. The involatile material obtained was pure by NMR. Yield: 3.0 g, 80%.

$^1$H NMR (CDCl$_3$): δ 1.12 (12H, dt J=1.16 Hz, 7.15 Hz; OCH$_2$C$\underline{H}_3$) 1.51 (4H, br m; PC$_2$H$_4$P), 1.7 (8H, br t, J=7.4 Hz; PC$\underline{H}_2$CH$_2$OEt), 3.4 (8H, dt J=1.16 Hz, 7.15 Hz, OC$\underline{H}_2$CH$_3$), 3.49 (8H; br m; PCH$_2$C$\underline{H}_2$OEt) ppm.

$^{31}$P NMR: δ −33.17 ppm.

Tetrofosmin was converted to Tetrofosmin sulphosalicylate by reaction with 2.3 to 2.5 molar equivalents of 5-sulfosalicyclic acid at room temperature in ethanol, followed by recrystallisation from ethanol/ether.

Example 2

Comparison of Formulations Having Varying Concentrations of Tetrofosmin, Ascorbic Acid and Sodium Hydrogen Carbonate The following lyophilised formulations were prepared:

| Sample | NaHCO₃ mg | mmoles | Ascorbic Acid (AA) mg | mmoles | Tetrofosmin (T) mg | mmoles | T:AA (molar ratio) |
|---|---|---|---|---|---|---|---|
| 1 | 11 | 0.13 | 3.0 | 0.017 | 1.5 | 0.0039 | 0.23:1.0 |
| 2 | 11 | 0.13 | 7.0 | 0.040 | 1.5 | 0.0039 | 0.10:1.0 |
| 3 | 24 | 0.29 | 7.0 | 0.040 | 1.5 | 0.0039 | 0.10:1.0 |
| 4 | 11 | 0.13 | 5.0 | 0.028 | 1.5 | 0.0039 | 0.14:1.0 |
| 5 | 11 | 0.13 | 3.0 | 0.017 | 3.0 | 0.0078 | 0.46:1.0 |
| 6 | 11 | 0.13 | 7.0 | 0.040 | 3.0 | 0.0078 | 0.20:1.0 |
| 7 | 24 | 0.29 | 7.0 | 0.040 | 3.0 | 0.0078 | 0.20:1.0 |
| 8 | 11 | 0.13 | 5.0 | 0.028 | 3.0 | 0.0078 | 0.28:1.0 |

Each of these formulations was reconstituted with 30 ml $^{99m}$Tc-pertechnetate (TcO$_4^-$) from a Drytec™ generator (GE Healthcare) with a radioactivity of 55 GBq to produce a radiopharmaceutical composition having 50 mCi/ml. 1 ml samples of the radiopharmaceutical composition were taken up into 3 ml PrecisionGlide (Becton Dickinson) syringes. The syringes were stored in a vertical position for 6 hours at room temperature in the dark. Following storage, each syringe was placed in a plastic tube and the activity of the whole syringe with the needle assembled was measured in an ion chamber (Canberra CRC 15R). The activity of the empty syringe was measured in the ion chamber. The needle was removed and the activity of the syringe was recorded without needle. The activities were adjusted for decay and the retained activity was calculated. The following results were found:

| Sample | Retained Activity on Syringe (%) |
|---|---|
| 1 | 9.8 |
| 2 | 10.1 |
| 3 | 10.0 |
| 4 | 10.6 |
| 5 | 7.1 |
| 6 | 7.8 |
| 7 | 7.2 |
| 8 | 6.8 |

Example 3

Comparison of Formulations Having Varying Concentrations of Tetrofosmin and Ascorbic Acid The following lyophilised formulations were prepared:

| Sample | NaHCO₃ mg | mmoles | Ascorbic Acid (AA) mg | mmoles | Tetrofosmin (T) mg | mmoles | T:AA (molar ratio) |
|---|---|---|---|---|---|---|---|
| 9 | 11 | 0.13 | 3.0 | 0.017 | 1.5 | 0.0039 | 0.23:1.0 |
| 10 | 11 | 0.13 | 5.0 | 0.028 | 1.5 | 0.0039 | 0.14:1.0 |
| 11 | 11 | 0.13 | 3.0 | 0.017 | 3.0 | 0.0078 | 0.46:1.0 |
| 12 | 11 | 0.13 | 5.0 | 0.028 | 3.0 | 0.0078 | 0.28:1.0 |
| 13 | 11 | 0.13 | 1.0 | 0.006 | 1.5 | 0.0039 | 0.65:1.0 |
| 14 | 11 | 0.13 | 1.0 | 0.006 | 3.0 | 0.0078 | 1.3:1.0 |
| 15 | 11 | 0.13 | 1.0 | 0.006 | 4.5 | 0.0117 | 2.0:1.0 |
| 16 | 11 | 0.13 | 2.0 | 0.011 | 1.5 | 0.0039 | 0.35:1.0 |
| 17 | 11 | 0.13 | 2.0 | 0.011 | 3.0 | 0.0078 | 0.70:1.0 |
| 18 | 11 | 0.13 | 2.0 | 0.011 | 4.5 | 0.0117 | 1.06:1.0 |
| 19 | 11 | 0.13 | 3.0 | 0.017 | 1.5 | 0.0039 | 0.23:1.0 |
| 20 | 11 | 0.13 | 3.0 | 0.017 | 3.0 | 0.0078 | 0.46:1.0 |
| 21 | 11 | 0.13 | 3.0 | 0.017 | 4.5 | 0.0117 | 0.69:1.0 |

These formulations were reconstituted, stored and the activity measured as described above for Example 2. RCP was measured by ITLC and PC at the time of reconstitution and at 24 hours post-reconstitution. The following results were obtained:

| Sample | Retained Activity on Syringe (%) | RCP 0 h | RCP 24 h |
|---|---|---|---|
| 9 | 13.5 | 95.9 | 90.3 |
| 10 | 10.7 | 95.5 | 91.7 |
| 11 | 8.3 | 95.6 | 92.9 |
| 12 | 8.5 | 95.6 | 93.4 |
| 13 | 8.6 | 95.6 | 88.4 |
| 14 | 7.5 | 95.6 | 91.6 |
| 15 | 7.6 | 94.0 | 94.3 |
| 16 | 8.0 | 93.4 | 88.7 |
| 17 | 7.5 | 95.5 | 92.5 |
| 18 | 5.9 | 93.6 | 94.1 |
| 19 | 9.1 | 95.5 | 90.8 |
| 20 | 6.7 | 94.7 | 92.7 |
| 21 | 5.3 | 95.6 | 93.1 |

Example 4

Radiopharmacy Comparison of Myoview™ with a Multi-Dose Kit of the Invention

The following lyophilised formulations were prepared:

| Formulation | Components | |
|---|---|---|
| Myoview ™ | tetrofosmin | 0.23 mg |
| | stannous chloride dihydrate | 0.03 mg |
| | disodium sulfosalicylate | 0.32 mg |
| | sodium-D-gluconate | 1.0 mg |
| | sodium hydrogen carbonate | 1.8 mg |
| | pH on reconstitution with saline | 8.3 to 9.1. |
| Multi-dose kit of the invention | tetrofosmin: | 1.38 mg |
| | stannous chloride dihydrate: | 0.09 mg |
| | disodium sulfosalicylate | 1.92 mg |
| | sodium D-gluconate: | 3.0 mg |
| | sodium hydrogen carbonate: | 11 mg |
| | ascorbic acid: | 3.0 mg |
| | pH on reconstitution with saline | 8.3 to 9.1. |

200 vials of each formulation were tested at 2 separate radiopharmacies. Reconstitution of the formulations was carried out using $^{99m}$Tc-pertechnetate (TcO$_4^-$) from a BMS generator. The Myoview™ formulation was reconstituted with 10 ml [18.5 GBq (500 mCi)], and the multi-dose kit of the invention was reconstituted with 30 ml [55.5 GBq (1500 mCi)]. 3 ml PrecisionGlide (Becton Dickinson) syringes were loaded with 1.0 ml of reconstituted formulation, avoiding air bubbles.

Each loaded syringe was stored vertically for 6 or 12 hours. Following storage, the syringe was placed in a plastic tube and the activity of the syringe was measured before and after emptying with the needle assembled, and after emptying without the needle assembled. The activity values were adjusted for decay.

The following values were obtained for Pharmacy 1:

|  | Activity | Storing | Retained Activity on Syringe (%) |
| --- | --- | --- | --- |
| Myoview ™ | ~1.0GBq (28 mCi)/ml | 6 h | 12.2 |
| Invention kit | ~1.0GBq (28 mCi)/ml | 6 h | 6.8 |
| Myoview ™ | ~0.5GBq (14 mCi)/ml | 12 h | 14.7 |
| Invention kit | ~0.5GBq (14 mCi)/ml | 12 h | 9.6 |

The following values were obtained for Pharmacy 2:

|  | Activity | Storing | Retained Activity on Syringe (%) |
| --- | --- | --- | --- |
| Myoview ™ | ~1.0GBq (28 mCi)/ml | 6 h | 11.4 |
| Invention kit | ~1.0GBq (28 mCi)/ml | 6 h | 6.7 |
| Myoview ™ | ~0.5GBq (14 mCi)/ml | 12 h | 14.5 |
| Invention kit | ~0.5GBq (14 mCi)/ml | 12 h | 11.4 |

The invention claimed is:

1. A radiopharmaceutical composition consisting essentially of:
   (i) a $^{99m}$Tc complex of tetrofosmin in a biocompatible carrier;
   (ii) non-radioactive tetrofosmin; and,
   (iii) a radioprotectant chosen from ascorbic acid or a salt thereof with a biocompatible cation;
   wherein the molar ratio of total tetrofosmin (i)+(ii) to radioprotectant (iii) is in the range 0.2:1.0 to 1.0:1.0, the concentration of said radioprotectant is in the range 0.3-0.6 mM, the pH of the composition is 8.0 to 9.2, and the concentration of total tetrofosmin is in the range 0.12-0.40 mM.

2. The radiopharmaceutical composition of claim 1 wherein said molar ratio of total tetrofosmin to radioprotectant is in the range 0.2:1.0 to 0.5:1.0.

3. The radiopharmaceutical composition of claim 1 which further comprises a biocompatible reductant.

4. The radiopharmaceutical composition of claim 3, where said biocompatible reductant comprises stannous ion.

5. The radiopharmaceutical composition of claim 1 which further comprises a pH adjusting agent.

6. The radiopharmaceutical composition of claim 5 where said pH-adjusting agent comprises sodium bicarbonate.

7. The radiopharmaceutical composition of claim 1, which further comprises 5-sulfosalicylic acid and gluconic acid or salts thereof with a biocompatible cation.

8. The radiopharmaceutical composition of claim 1, wherein the radioprotectant is ascorbic acid.

9. The radiopharmaceutical composition of claim 1, wherein the biocompatible carrier comprises saline solution.

10. A unit patient dose of the radiopharmaceutical $^{99m}$Tc-tetrofosmin which comprises the radiopharmaceutical composition of claim 1 in a clinical grade container or syringe, wherein the $^{99m}$Tc radioactive content of the radiopharmaceutical is suitable for imaging a single patient.

11. The unit patient dose of claim 10, which is provided in a syringe having a syringe shield to protect the operator against radiation dose.

12. A process for the preparation of multiple unit patient doses of the radiopharmaceutical $^{99m}$Tc-tetrofosmin, which comprises:
   (i) reconstituting a lyophilized formulation consisting essentially of:
      (a) tetrofosmin; (b) a radioprotectant chosen from ascorbic acid or a salt thereof with a biocompatible cation; and, (c) a biocompatible reductant; wherein the molar ratio of tetrofosmin to radioprotectant is in the range 0.2:1.0 to 1.0:1.0, the concentration of said radioprotectant is in the range 0.3-0.6 mM, and the concentration of tetrofosmin is in the range 0.12-0.40 mM, with either a sterile solution of $^{99m}$Tc-pertechnetate or first a biocompatible carrier followed by a sterile solution of $^{99m}$Tc-pertechnetate;
   (ii) allowing $^{99m}$Tc-tetrofosmin complex formation to take place to give a solution comprising a bulk supply of the desired $^{99m}$Tc-tetrofosmin radiopharmaceutical;
   (iii) optionally checking the radiochemical purity of the bulk supply of the $^{99m}$Tc-tetrofosmin complex;
   (iv) withdrawing a unit dose from the bulk supply of step (iii) into a plastic syringe or container;
   repeating step (iv) with an additional plastic syringe or container at later times to give further unit doses.

13. The process of claim 12, wherein the $^{99m}$Tc-pertechnetate used in step (i) has a radioactive content in the range 0.2 to 100 GBq.

* * * * *